United States Patent [19]
Lehmann et al.

[11] Patent Number: 5,365,776
[45] Date of Patent: Nov. 22, 1994

[54] PROCESS AND DEVICE FOR DETERMINING THE VISCOSITY OF LIQUIDS

[75] Inventors: Jochen K. Lehmann, Rostock; Roland Glatzer, Bad Schwalbach; Jutta Hartmann, Weiterstadt; Dieter Wagner, Wiesbaden, all of Germany

[73] Assignee: Schott Gerate GmbH, Hofheim, Germany

[21] Appl. No.: 86,168

[22] Filed: Jul. 6, 1993

[30] Foreign Application Priority Data

Jul. 6, 1992 [DE] Germany ............................ 4222111
Jun. 23, 1993 [DE] Germany ............................ 4320813

[51] Int. Cl.$^5$ ........................................... G01N 11/06
[52] U.S. Cl. ................................................ 73/54.07
[58] Field of Search ............... 73/54.07, 54.08, 54.09, 73/54.04

[56] References Cited

U.S. PATENT DOCUMENTS

| | | | |
|---|---|---|---|
| 1,973,297 | 9/1934 | Shearer | 73/54.04 |
| 2,048,305 | 7/1936 | Ubbelohde | 73/54.07 |
| 2,238,758 | 4/1941 | Thornhill | 73/54.07 |
| 4,893,500 | 1/1990 | Fink-Jensen | 73/54.37 |

FOREIGN PATENT DOCUMENTS

| | | | |
|---|---|---|---|
| 2221993 | 10/1974 | France . | |
| 2338487 | 8/1977 | France . | |
| 2559906 | 8/1985 | France | 73/54.07 |
| 39777 | 6/1965 | German Dem. Rep. . | |
| 2115396 | 10/1971 | Germany . | |
| 3331659 | 4/1985 | Germany . | |
| 3690367 | 8/1987 | Germany . | |
| 3611867 | 10/1987 | Germany . | |
| 3712394 | 10/1987 | Germany . | |
| 116036 | 7/1984 | Japan | 73/54.07 |
| 87/00626 | 1/1987 | WIPO . | |
| 8700626 | 1/1987 | WIPO | 73/54.07 |

OTHER PUBLICATIONS

Umstätter, Einführung in die Viskosimetrie und Rheometrie, Springer-Verlag, p. 90 (1952).
ASTM D 446-89a (1989).
DIN 53 177 (Jul. 1974).

*Primary Examiner*—Thomas P. Noland
*Assistant Examiner*—Joseph W. Roskos
*Attorney, Agent, or Firm*—Millen, White, Zelano & Branigan

[57] ABSTRACT

A process and a device for determining the viscosities of liquids are described, which work quickly, reliably and accurately. The process according to the invention makes use of the fact that disturbing effects are eliminated when measuring the change in the rate of flow of the liquid from the viscometer, while utilizing the change in the hydrostatic pressure during viscosity measurement and that the viscosities can be reliably determined from the measured data by the Hagen-Poiseuille law. The viscometer according to the invention is designed so that the hydrostatic pressure change during measurement is maximal.

17 Claims, 6 Drawing Sheets

PROCESS AND DEVICE FOR DETERMINING THE VISCOSITY OF LIQUIDS

SUMMARY OF THE INVENTION

The invention relates to a process and a device for determining the viscosity of liquids with a capillary viscometer, comprising a storage vessel and a capillary tube.

The resultant viscosity measured is, optionally, either the kinematic or the dynamic viscosity.

Viscosities of liquids are usually determined with capillary viscometers according to Ostwald or according to Ubbelohde. A modern representation of these devices is provided in: A. Nagashima, J. V. Sengers, W. A. Wakeham: Experimental Thermodynamics, Vol. III: "The Measurement of Transport Properties of Fluids," Blackwell, Oxford 1991.

Capillary viscometers described therein work by providing a liquid above a capillary and the liquid passes through the capillary by hydrostatic pressure. The liquid is in a generally spherical vessel, to which cylindrical tubes are connected above and below. There are reference marks on each of the cylindrical tubes. When the liquid meniscus passes these reference marks, a time measurement takes place manually or electronically in each case. The time required for the meniscus of the liquid to pass between the two reference marks is a measurable variable.

In the known viscometers, a spherical vessel is used for the purpose of keeping the hydrostatic pressure, which is dependent on the level of the column of liquid in the capillary and in the storage vessel, substantially constant during the measurement. By enlarging the inner volume of the spherical vessel, even the passage of a sizeable mass of liquid flowing therethrough results in only a comparatively small change in the level of the upper meniscus of the column of liquid and thus does not induce too great a change in the hydrostatic pressure.

In the above-described measurement of the time required to pass the reference marks, the continuous change in the driving hydrostatic pressure is not taken into consideration. Only an average value of the pressure between the two reference marks is considered and it is this average value which enters into the evaluation as driving pressure.

With the known viscometers, viscosities can be determined with relatively high accuracy. However, the measurements are very time-consuming. Thus, at least 20 minutes are required, e.g., for the measurement of oils with an Ubbelohde viscometer. Such viscometers are not advantageous for the performance of quick measurements, such as are required, e.g., in the input-/output control of mineral oil products in refineries.

An object of the invention, therefore, is to make available a process and a device for determining the viscosity of liquids, which provide quick and reliable results with comparatively high accuracy.

Upon further study of the specification and appended claims, further objects and advantages of this invention will become apparent to those skilled in the art.

These objects are achieved with respect to the process of determining viscosity using a capillary viscometer by measuring the change in the rate of flow of the liquid whereby the viscosity of the liquid can be determined from the measured data using the Hagen-Poiseuille law. A suitable device is a capillary viscometer comprising a storage vessel and a capillary tube, wherein dimensions of said storage vessel and capillary tube are selected to achieve a maximal change in hydrostatic pressure during viscosity measurement.

The process according to the invention makes use especially of the usually undesirable change of the pressure level during measurement for the determination of viscosity. That this approach of using an effect previously considered a disadvantage leads to success is completely surprising to one skilled in the art. As was already initially stated, previously all typical capillary viscometers were designed so as to avoid as much as possible during the measurement the effect, considered disturbing, of the change in hydrostatic pressure. In many cases, this goal was at least approximately achieved, for example, in the case of the above-mentioned Ubbelohde-Ostwald viscometers. Where this goal was not achieved, such as, e.g., in the so-called reverse flow viscometers, makeshift measures have to be used even with different working constants for one and the same viscometer, as a function of the pressure level change being produced during the measurement. See, e.g., ASTM D 446–89a (1989).

Another possibility to eliminate the pressure level change during the measurement is the use of separate pressure, which is used, e.g., in Ubbelohde viscometers of the isosceles design or else in the case of Ostwald viscometers of specific design. See, e.g., DIN 53 177 (Jul. 1974).

But in all known cases, the pressure difference between the beginning of measurement and the end of measurement, which is always still present despite all measures, was considered a disadvantage. That this same pressure difference, considered a drawback in known processes, can be used to successfully determine viscosity is completely unexpected.

In the tests which resulted in the invention, it was found that the continuous change of the driving pressure can be evaluated not only to determine viscosity but that as a result even disturbance variables can be eliminated, which previously resulted in uncertainties in capillary viscometry (e.g., the change in hydrostatic pressure which was not previously taken into account). This occurs because the changing ratio of outflowing mass to time characteristically depends on the viscosity of the measuring liquid. For this purpose, several possibilities for evaluation were found.

According to the invention, depending on the field of use, three different processes for determining the change in the rate of flow are preferred:

1. The measurement of the change in mass of liquid flowing out of the capillary viscometer as a function of time;
2. The measurement of the sequence of drops of liquid exiting from the capillary viscometer as a function of time, and optionally also detection of the draining process; and
3. The measurement of the level change of the liquid meniscus in the storage vessel as a function of time.

The evaluation of these measurements for determining the viscosity coefficients of a liquid is described below by the example of measuring the change in mass flowing out per unit of time (process 1). As will become evident below, this type of evaluation can easily be applied to processes 2 and 3, as well as other methods for determining the time change in the rate of flow, by slight modification of the equations presented below.

In the following, it is possible, with the process and the device of the invention, to obtain an automatic continuous tracking or monitoring of the measured value "mass as a function of time," which is then evaluated using the functional correlation "dm/dt=f(m)." This type of measurement takes into account very well the physical fact that the hydrostatic pressure of the column of liquid decreases with the decreasing level of the column of liquid.

The correlation between mass and time, which is given by the flow of the liquid through the capillary, can be described with the Hagen-Poiseuille law:

$$\frac{dv}{dt} = \frac{\pi \cdot r^4 (p_1 - p_0)}{8\eta l} \tag{1}$$

wherein
dv/dt is the volume per unit of time passing through the capillary tube,
r is the radius of the capillary tube,
($p_1-p_0$) represents the pressure difference between the upper and lower ends of the capillary,
$\eta$ is the dynamic viscosity coefficient of the liquid, and
l is the length of the capillary tube.

Both volume v and the driving pressure p can be represented as a function of mass m of the liquid. For the volume, the equation $$v = \frac{m}{\rho} \tag{2}$$

(wherein v is volume, m is mass of the liquid and p is density of the liquid) is obtained. For the pressure of the column of liquid in the storage vessel having a cross-sectional area A above the capillary, the equation $$p_1 = \frac{mg}{A} + p_0 \tag{3}$$

(wherein $p_1$ is the pressure at the upper end of the capillary tube, m is the mass of the column of liquid in the storage vessel, g is acceleration due to gravity, A is the cross-sectional area of the storage vessel, and $P_0$ is the pressure at the lower end of the capillary tube) is obtained.

Since hydrostatic pressure $p_1$ of the column of liquid and thus the driving pressure decreases as the liquid flows out, a functional correlation is produced from equations (1), (2) and (3) in the form $$\frac{dm}{dt} = km \tag{4}$$

with $$k = \frac{\pi r^4 g \rho}{8\eta l A} \tag{5}$$

or with $$k = \frac{r^4 g \rho}{8\eta l R^2} \tag{7}$$

(R is the radius of the storage vessel).

It has been found by experiments that in making a viscosity measurements in the above-described way, corrective term values emerge due to the nonideality of the experimental procedure which, in equation (4), have the effect of an additional constant mass. Thus, equation (4) changes to $$\frac{dm}{dt} = km + c \tag{8}$$

in which constant c is the sum of additive correction term values.

If the parameters of the capillary tube are constant (length l, radius r) and cross-sectional area A of the storage vessel is constant, the viscosity coefficient of the liquid flowing through is decided by the value of the proportionality factor k and thus can be determined from the measured values.

If the apparatus parameters of capillary tube length l, capillary tube radius r as well as cross-sectional area A or radius R of the storage vessel are known, kinematic viscosity coefficient v can be determined from k using the following equation:

$$v = \frac{\eta}{\rho} \tag{9}$$

Apparatus parameters l, r, A or R are determined absolutely or determined by calibration on a liquid of exactly known viscosity (e.g., water). Further, if the density of the liquid is known, the dynamic viscosity coefficient can be determined from equation (9).

Because of the occurrence of constant c in differential equation (8), the usual evaluation of this type of equation is impeded by an integration. The method is therefore preferably selected to differentiate measured values "m=f(t)" and to evaluate the differentiated form as linear equation (8). The differentiation is facilitated by the fact that almost any large number of experimental value pairs can be made available because of the continuous evaluation of the measurement. The differentiation can take place, for example, according to a process of R. Ludwig: "Methoden der Fehler- und Ausgleichsrechung", ["Methods of Computation of Errors and Lease Squares Adjustment"], VEB DVW, Berlin 1969.

The above-described type of evaluation is suitable not only for process 1, but also for the evaluation of the measurement of the sequence of drops with optionally also detecting the draining process. By detection of the draining process, it is to be understood that what is meant is determination of the drop shape and size. It has turned out that the drop size remains almost constant during the entire measurement, i.e., it is a function of the surface tension and the draining tip of the capillary viscometer, but not of the change of the hydrostatic pressure in the column of liquid. By knowing the size or shape of drops having a known density, the drop mass and thus the mass flowing out per unit of time can be determined by observation of the sequence of drops. When the drop size is not constant, their volumes can be determined by monitoring the size and/or shape of the drops and, if the density of the liquid is known, the mass of the drops can also be determined.

To evaluate the measurements of the sequence of drops (without mass determination) or the change in the level of the column of liquid as a function of time (processes 2 and 3), equation (8) together with equation (2) can be converted in a simple way to a volume change. In this case, volume v takes the place of mass m in equation (8).

In the measurement of the sequence of drops as a function of time, the time is recorded at which a drop passes through a predetermined measuring point. Obviously, this measuring point should be the same for all drops for the sake of simplicity. To detect the passage of a drop through the measuring point, for example, suitable optical scanning devices, such as, e.g., light barriers or devices for image analysis (=e.g., CCD-lines) can be used.

The number of measuring points, i.e., the number of "detected" drops, depends on the desire measuring accuracy. It has been determined that, with the measurement of about 10 drops, very good results can be achieved. Furthermore, this results in very short periods for performing the measurements. Generally, 20 seconds are required for a measurement. The short measuring times apply generally to the process according to the invention and are independent of the manner in which the change in the rate of flow of the liquid is detected by the viscometer (processes 1 to 3).

The determination of the change in the level of the column of liquid (or of the upper liquid meniscus) in the storage vessel as a function of time can advantageously occur by subdividing the storage vessel in the measuring area into preset lengthwise sections, which each correspond respectively to the same liquid volume, for example, by using the sections of the same length with a cylindrical precision pipe as the storage vessel and with suitable measuring devices, such as, e.g., light barriers, camera lines and diode arrays. In each case, the length of time for the passage of the liquid meniscus through each lengthwise section is measured. In this type of measurement, as in the case of determining the sequence of drops, curves can be plotted, volume change per time dv/dt as a function of volume v, from whose ascending slope viscosity coefficients can be determined according to equation (7) and the above-described evaluation with respect to the apparatus constants. In this way, knowledge of the drop volumes or of the liquid volumes, which are enclosed in the preset lengthwise sections, is not necessary, as long as these volumes are constant during the measurement, as is the case in the described process.

The above-described processes for measuring the change in the rate of flow of the liquid through the viscometer are preferred procedures and are not the only ones possible. Given the knowledge of the general process aspect of the invention, one skilled in the art can then easily recognize a series of other procedures, which are also suitable for measuring the change in rate of flow, for example, procedures matched to specific applications.

Faced with the object of finding a capillary viscometer suitable for carrying out the process according to the invention, the approached used by one skilled in the art will generally be to first select a suitable capillary tube diameter for the viscosity range of interest to him, based on known data collections for viscometry, for example, DIN standard 51 562. The diameter of the storage vessel, of course, has to be larger than the diameter of the capillary tube, to ensure that the change in hydrostatic pressure is measurable during the measurement. If the capillary tube and storage vessel have the same diameter, the frictional force and the driving pressure will approximately balance each other out and the liquid will flow through the capillary at a steady rate. The greater the diameter of the storage vessel is in comparison to the diameter of the capillary, the greater the measurable effects will be.

The change in the rate of flow initially becomes greater with increasing diameter of the storage vessel. As the storage vessel diameter increases further, the change in the rate of flow eventually passes through a maximum value and then with even greater diameter of the storage vessel, will finally become so small again that it cannot be measured. This is to be attributed to the fact that with a very large diameter of the storage vessel in comparison to the capillary, the hydrostatic pressure, similar to the way it is in the known viscometers with enlarged lengthwise section in the measuring area of the storage vessel, changes only insignificantly when a preset liquid volume passes through the capillary. One of ordinary skill in the art can determine by routine experimentation ratios of capillary tube diameter to storage vessel diameter which will achieve a maximum effect in the change in the rate of flow.

In general, the dimensions of the viscometer, e.g., the diameter ratio of the storage vessel to the capillary tube, are preferably selected so that a maximum effect occurs in the change in the rate of flow. In addition, the accuracy of the timing plays a large role. In the usual applications, diameter ratios of preferably about 1:1.5–1:50 for capillary:storage vessel are especially advantageous. Also, the timing accuracy should generally be better than about 1/10 of a second to achieve sufficiently accurate measuring results.

The length of the capillary affects the rate of flow. The longer the capillary tube is, the more slowly the liquid flows through the viscometer.

The length of the storage vessel also influences the rate of flow: the higher the column of liquid standing above the capillary is, the higher the driving hydrostatic pressure. It follows from the above that, especially if a drainage of the liquid in drop form from the capillary tube is desired and not a continuous flow, the length of the storage vessel (which in general is matched to the level of the column of liquid) should not be too large. On the other hand, the storage vessel has to be sufficiently high to hold a sufficient amount of liquid, when measuring the mass change or measuring the level change of the column of liquid as a function of time, so that many lengthwise sections of preset volume within the storage vessel can be monitored during the measurement of the change in rate of flow. It has turned out that in a viscometer for measuring viscosity coefficients in the range of about 0.5 mm$^2$/s - 10 mm$^2$/s with a capillary viscometer of r=0.2 mm and a capillary length of 20 mm or a diameter of the storage vessel of 2.5 mm, generally a length of the storage vessel in the range of about 10–15 cm is advantageous. In the case of a storage vessel of these dimensions, about 10 measuring points (i.e., 10 lengthwise sections) at regular intervals of 10 mm can be installed, which assure a sufficiently accurate and secure determination of the viscosity.

Also, in a measurement of the change in the rate of flow by monitoring the mass flowing out of a viscometer, as described above, the storage vessel should be high enough to hold at least 2 g of the liquid, to assure here, too, a sufficient accuracy of the measurement.

The above explanations show that in selecting suitable dimensions for a capillary viscometer for use in accordance with the invention, a multiplicity of factors should be considered. In particular, opposite effects can occur in the selection of the parameters. However, in general, sufficiently large ranges exist for the selection of dimensions, within which advantageous results can be achieved, so that one skilled in the art, with a few routine experiments or calculations of his own, can readily determine a viscometer optimally made for his desired use.

The process according to the invention has the advantage that it allows a quick and reliable determination of viscosities of liquids, and a relatively high measuring accuracy is assured. It can therefore be used, e.g., for the input/output control for mineral oil products. The viscometer according to the invention is distinguished, as is also shown below in the description of the figures, by a very simple, stable design.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
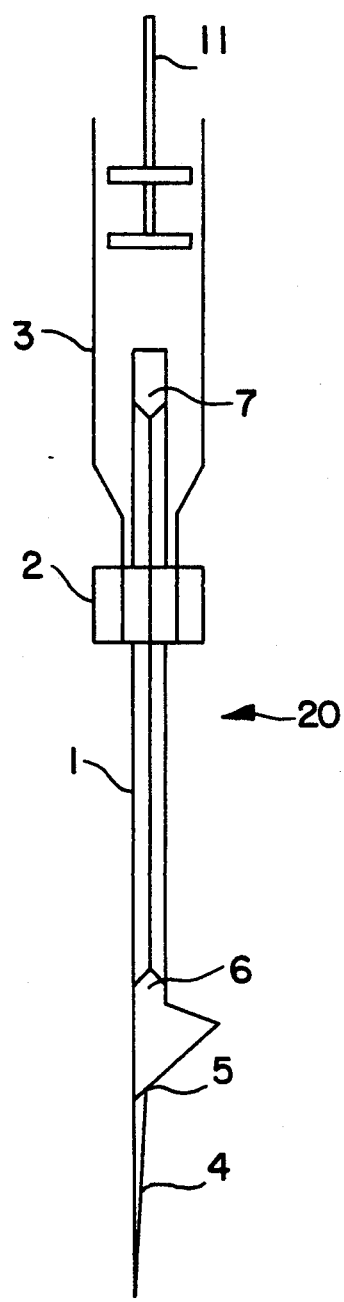
FIG. 1 illustrates a configuration of a capillary viscometer according to the invention.

In a diagrammatic representation, FIG. 1 shows a viscometer (20) according to the invention having a storage vessel (3) and a capillary tube (1). The tempering device, a device which serves to keep temperature constant during measurement, necessary for high-accuracy viscosity measurements is not the object of the described invention and is not shown in FIG. 1.

Figure 5:
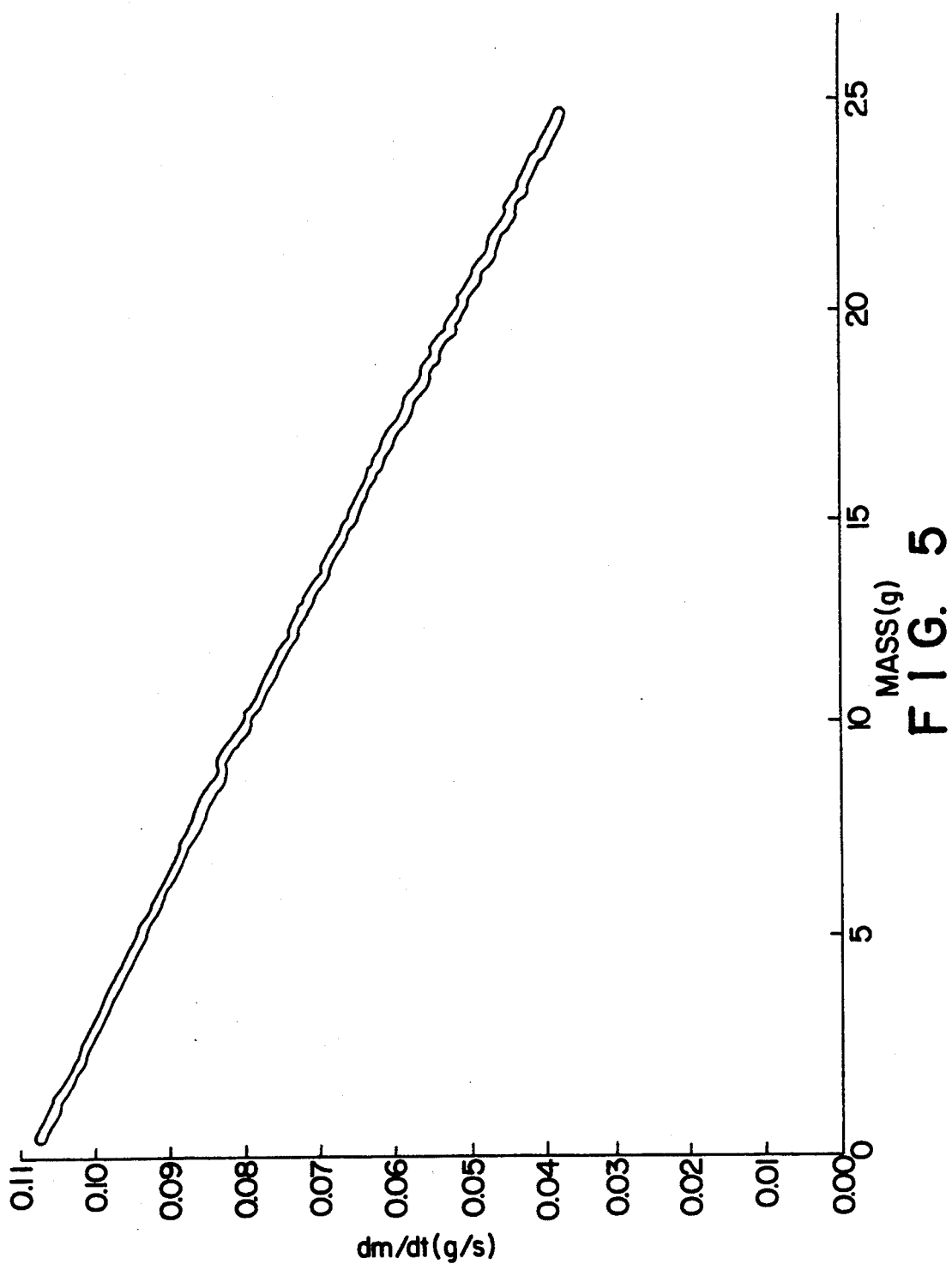
FIG. 5 illustrates a graphical representation of the differential change of the ascending slope of measuring curve m=f(t) of FIG. 4 as a function of the mass.
Figure 6:
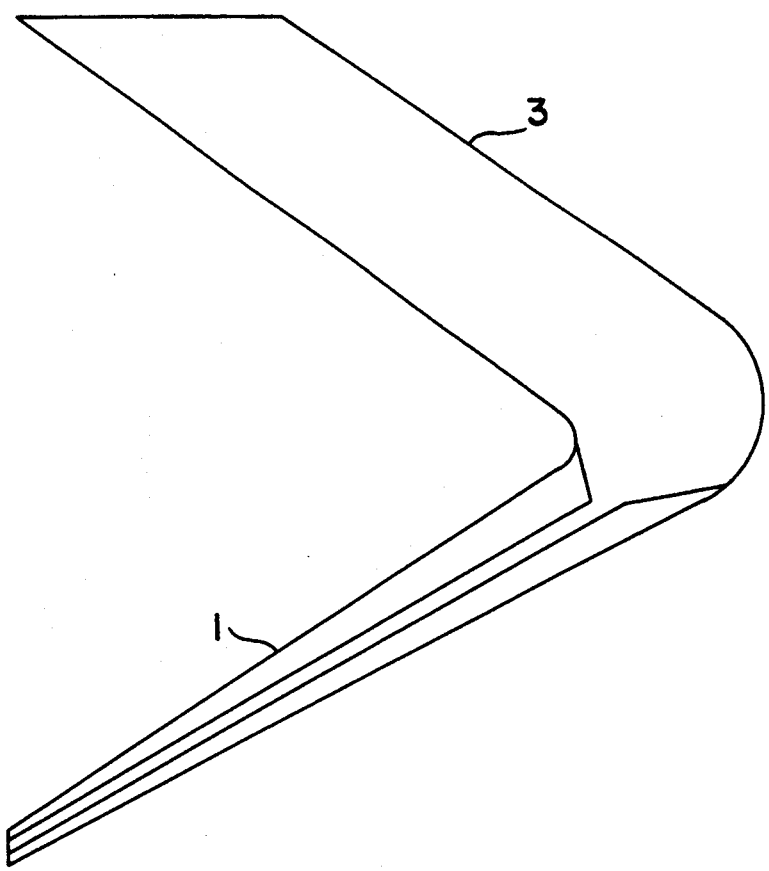
FIG. 6 illustrates an embodiment where the axis of the storage vessel and/or the axis of the capillary tube are at an angle to the perpendicular.

The preferred shape of storage vessel (3) is cylindrical. However, other shapes can be desirable for other evaluations. For example, if the cross-section of the storage vessel defined at one or more points changes, then a straight line according to FIG. 5 is not obtained, but instead a graph exhibiting successive straight lines offset parallel is obtained. Each of the steps in the graph developed in this manner corresponds exactly to a point on storage vessel (3), at which the cross-section changed.

Changes in the cross-section change can also be achieved by introducing a molded element (11) from above into the storage vessel (3), which by its shape causes a change in the effective cross-section at defined points within the storage vessel (3).

By using cross-section changes applied an different intervals, it is possible to place reference marks in the obtained measuring curve which characterize the flow of a defined volume of liquid. In this way, it is possible to place the mass of the discharged liquid with its volume in a ratio and determine the density of the liquid. Another possibility for determination of the volume in storage vessel (3) takes place by two light barriers, which delimit a defined volume.

The invention is thus by no means limited to cylindrically shaped storage vessels (3). Depending on the use, other shape variants can also be advantageously employed.

Storage vessels with other shape variants can be advantageous for measurements of liquids with non-Newtonian flow behavior. Here, e.g., funnel-, bell- or trumpet-shaped storage vessels can be used for this purpose to vary within routine measurements the curves according to FIG. 5 (at first nonlinear), resulting for these cases, to straight lines.

The shape of capillary (1) is normally straight, and the inner diameter is constant over the entire length. But to be able to influence the ratio of pressure level to capillary length and diameter, other shapes are also provided, which are bent, e.g., spiral-, saw-tooth- or step-shaped.

With respect to the connection (2) between storage vessel (3) and capillary tube (1), two possibilities are provided depending on requirement, flexibility and sample yield: a permanent connection, e.g., a fusing or a gluing; or a replaceable connection, e.g., with threaded joints or else with tubes (e.g., capillary tube is inserted in an opening in the bottom of the storage vessel providing a tight fitting therewith).

The shape of intake and/or outlet (7, 6) of the capillary tube is a relevant factor for most measurements. Intake (7) is normally funnel- or trumpet-shaped to assure a laminar flow behavior. The same applies to an increased extent to outlet (6). Other shapes of intake and/or outlet (7, 6) can significantly influence the course of measurement. Thus, e.g., a draining nip molded cone-shaped directly at the end of the capillary causes a very uniform drop formation. On the other hand, a sizable molded-on trumpet can produce an especially uniform pattern.

Since the surface tension has a great effect on the draining process, speed and informative value of the result can be greatly influenced by the shape of capillary outlet (6). One possibility for generally avoiding the drops is to immerse capillary (1) or a part added to it in a liquid.

For practical reasons, in some cases it may be necessary for storage vessel (3) and capillary (1) to be placed at any angle to one other or else to be used in a non-perpendicular position. Preferably, the viscometer (20) is used in perpendicular position, the axes of storage vessel (3) and capillary (1) being the same. The materials used for manufacturing the viscometer are basically determined by the corrosion expected from the measuring liquid. Preferably, glass is used, especially borosilicate glass 3.3. But also other materials, such as, e.g., metals or plastics, can be used.

Capillary tube (1) in FIG. 1 is connected by a screw/-crimp connection (2) with storage vessel (3) so that the capillary tube projects into the cylindrical part of storage vessel (3). The continuous outflow of the liquid from storage vessel (3) ends at this position. Such an arrangement is advantageous with respect to the Couette adjustment.

Capillary tube (1) is replaceable by screw/crimp connection (2) and the device is easy to detach and to clean.

Figure 2:
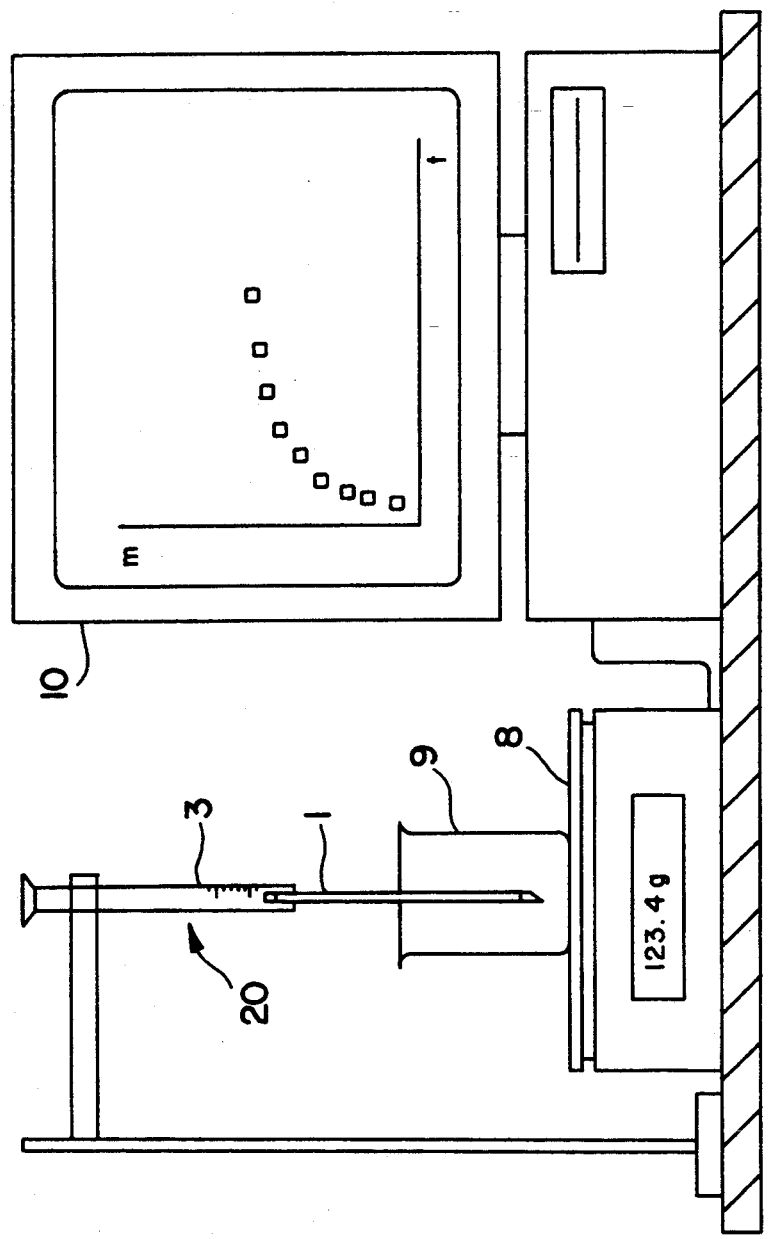
FIG. 2 illustrates a measuring arrangement with stationary viscometer according to FIG. 1.
Figure 3:
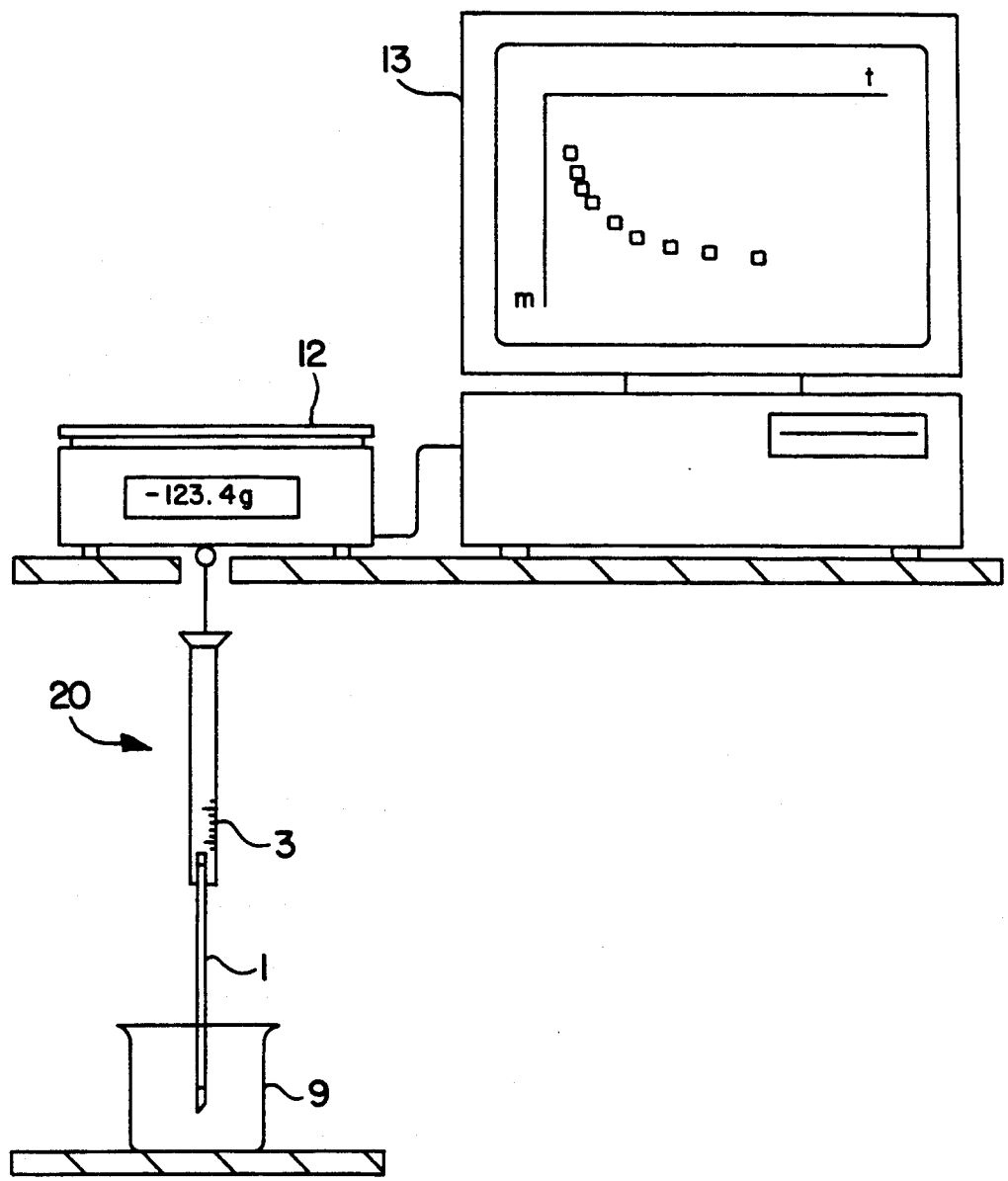
FIG. 3 illustrates a measuring arrangement with suspended viscometer according to FIG. 1.

FIG. 2 and FIG. 3 show a measuring arrangement with a viscometer (20) that is stationary or suspended on scales in connection with an electronic scale (8, 12) and a computer.

In the stationary arrangement of FIG. 2, the amount of flow is measured by weighing the amount of liquid flowing out of the viscometer, which flows onto a weighing device (8) located below viscometer (20).

In the suspended arrangement of FIG. 3, measurement of the amount of flow takes place by monitoring the reduction in the mass of viscometer (20), filled with sample liquid, which is suspended from a weighing device (12).

As scales, especially analytical balances with an accuracy of better than 1 mg are suitable.

Intake (7) of capillary tube (1) is of enlarged cone-shape to assure a laminar flowing in of the liquid into capillary tube (1). Outlet (6) of capillary tube (1) is also of enlarged cone-shape for the same reason, but ends in a laterally bevelled, trumpet-shaped opening (5). This, together with pull-off tip (4), guarantees the formation of the smallest possible drops.

Pull-off tip (4), as represented in FIGS. 2 and 3, can also be immersed in a liquid reservoir of a vessel (9), by which a continuous outflow of the liquid passing through capillary tube (1) is provided. The ascending force of pull-off tip (4) can be kept negligibly small with sufficiently fine shaping. This configuration is advisable especially if the measurement of the change in the rate of flow is to take place by weighing the amount of liquid flowing out from viscometer (20).

For the drop formation, on outlet end (6) of capillary tube (1), the back-diffusion-free metering and titrating tip known from DE-PS 32 27 955.8 is especially suitable. With use of this tip, drop formation occurs outside the capillary area. A reaction of the drop distorting the measuring result in the column of liquid in capillary viscometer (20) is thus avoided.

Instead of the scales, other weighing or force-sensing devices can also be used. An additional optical scanning can improve the detection of the draining liquid. Such devices are, e.g., as already described above, light barriers or devices for image analysis for the detection of the sequence of drops or of the entire draining process. Sequence of drops, drop shape and size can be important data for the evaluation. In the simplest case, the assumption is that the drops are the same size, which can result, e.g., for routine measurements, in limited requirements on the measuring resolution of the weighing device, since several drops can be weighed collectively.

For the numerical evaluation, instead of a commercially available computer, any other suitable evaluating device, e.g., an evaluating unit with a built-in microprocessor, can also be used.

EXAMPLE

Viscosity measurements on water were performed using a capillary viscometer made of borosilicate glass according to FIG. 1 with the following dimensions:

| | |
|---|---|
| Capillary tube | |
| Diameter (inner) | 0.6 mm |
| Length | 100 mm |
| Storage vessel | |
| Diameter (inner) | 30 mm |
| Length | 150 mm |
| Length of the section of the capillary projecting into the storage vessel | 20 mm |
| Outlet tip | 35 mm |

-continued

| | |
|---|---|
| Length | |

The measurements were performed using a "stationary" viscometer according to FIG. 2. An analytical balance of Sartorius A 210 S type with data output was used. The weighing accuracy was better than 1 mg. The evaluation was performed by a computer of IBM/PS 2 type, model 80, the timing took place inside the computer with a time resolution better than 1/10 sec.

Figure 4:
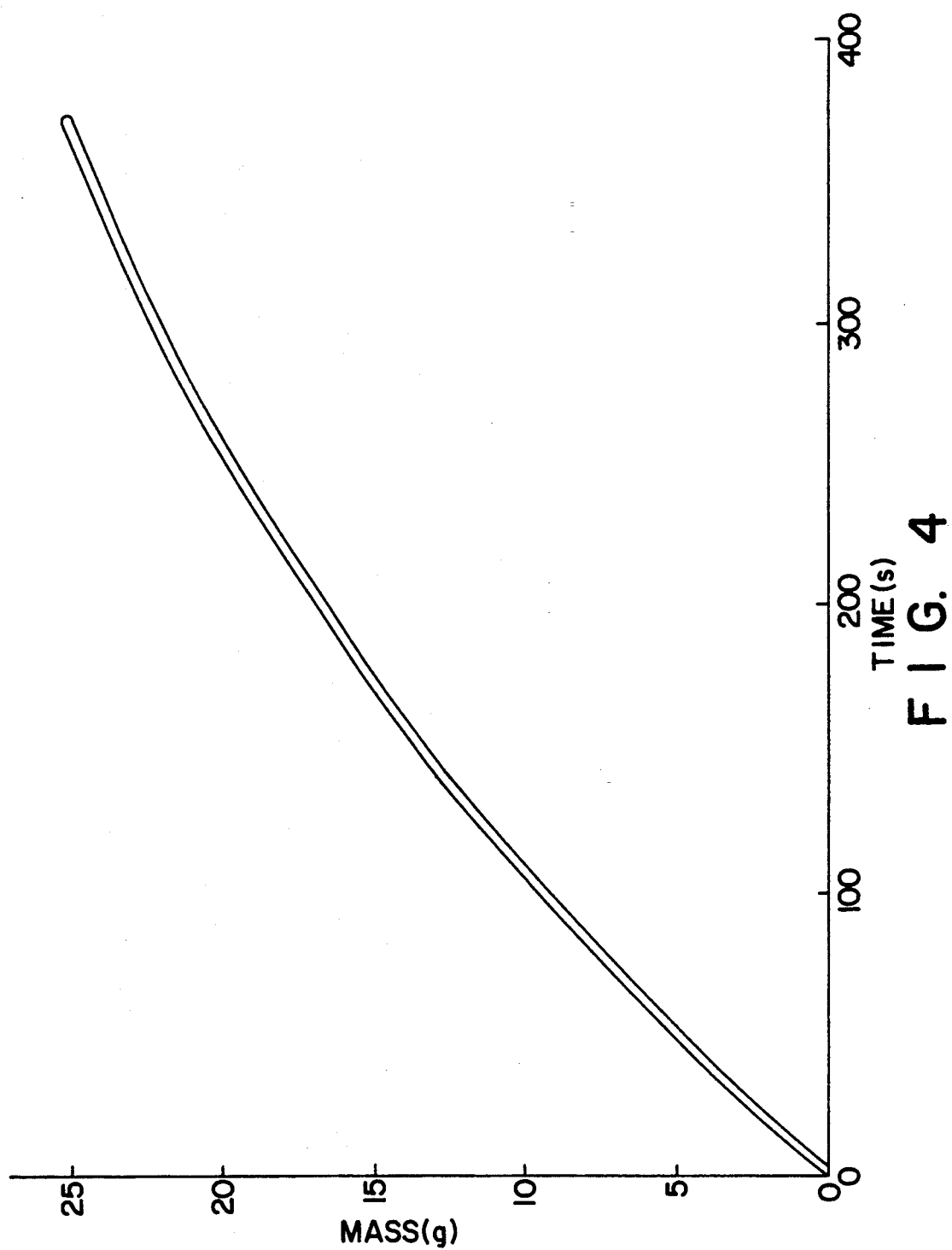
FIG. 4 illustrates a graphical representation of a measuring curve m=f(t)

FIG. 4 shows measured curve "m=f(t)." The curve produced in the measuring arrangement with a suspended viscometer according to FIG. 3 is analogous and corresponds to the reflection of the above-mentioned curve on the t-axis.

FIG. 5 shows the curve, which is produced according to the numerical differentiation of curve "m=f(t)." The straight line obtained corresponds to the result of the initially represented mathematical derivation and thus confirms the theory based on the above-described measuring principle. From the slope of the straight line, with knowledge of the constants of the capillary viscometer, the kinematic viscosity coefficient can be calculated and, with knowledge of the density of the liquid, the dynamic viscosity coefficient of the liquid can also be calculated.

The density of the measuring liquid can also be termined directly during the determination of the viscosity by the described variations of storage vessel (3).

It has further been observed that the curves run in a different shape if the measuring samples exhibit non-Newtonian flow behavior. For the measurement of such liquids, viscometers with very large storage vessel length (3) are an advantageous arrangement, in which optionally variable additional pressure can be used. By applying additional pressure, the mass flow out of the viscometer can be accelerated.

The preceding can be repeated with similar success by substituting the generically or specifically described operating conditions of this invention for those used.

Without further elaboration, it is believed that one skilled in the art can, using the preceding description, utilize the present invention to its fullest extent. The preferred specific embodiments are, therefore, to be construed as merely illustrative, and not limitative of the remainder of the disclosure in any way whatsoever.

The entire disclosure of all applications, patents and publications, cited above, and of corresponding German applications P 42 22 111.0 (filed Jul. 6, 1992) and P 43 20 813.4 (filed Jun. 23, 1993), are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for determining the viscosity of a Newtonian liquid with a capillary viscometer, comprising a storage vessel and a capillary tube, wherein said liquid flows from said storage vessel through said capillary tube, the improvement wherein:

the flow rate of liquid through said capillary tube changes with time, and the change in the rate of flow of liquid through the viscometer is measured whereby viscosity of the liquid can be determined by the Hagen-Poiseuille law, 2. A process according to claim 1, wherein the dimensions of said viscometer are selected to achieve a maximal change in hydrostatic pressure during the measurement.

3. A process according to claim 2, wherein the ratio of capillary tube diameter to storage vessel diameter is 1:1.5–1:50.

4. A process according to claim 1, wherein, in measuring the change in the rate of flow of liquid, the mass of liquid flowing out of the viscometer as a function of time is measured.

5. A process according to claim 4, wherein the measurement of the mass of the liquid flowing out per unit of time is performed by suspending said viscometer filled with said liquid on a weighing means and measuring the reduction of the mass of said viscometer.

6. A process according to claim 4, wherein measurement of the mass of the liquid flowing out per unit of time is performed by weighing, on a weighing means positioned below said viscometer, the amount of liquid flowing out of said viscometer.

7. A process according to claim 4, wherein measurement of the mass of the liquid flowing out per unit of time is performed by measuring the sequence of drops of the liquid exiting said viscometer as a function of time and simultaneously measuring the mass of said drops.

8. A process according to claim 4, further comprising measuring the density of said liquid wherein said storage vessel of said viscometer exhibits changes in cross-section which define preset liquid volumes, and whereby changes in the mass flow are produced for measuring the mass of the corresponding liquid volumes.

9. A process according to claim 1, wherein, in measuring the change in the rate of flow of liquid, the length of time required for each of a plurality of preset liquid volumes required to pass through preset measuring points is measured.

10. A process according to claim 9, wherein the sequence of drops of liquid exiting from the capillary viscometer is measured as a function of time.

11. A process according to claim 9, wherein the change of level of the liquid meniscus in the storage vessel is measured as a function of time.

12. A process according to claim 1, wherein the measured values are evaluated in the differential form $$\frac{dX}{dt} = k \cdot X$$

wherein $$\frac{r^4 \cdot g \cdot \rho \cdot \pi}{8 \cdot \eta \cdot A \cdot l};$$

13. A process according to claim 1, further comprising plotting and evaluating the measurements by a computer linked with a measuring device for obtaining said measurements.

14. A capillary-viscometer comprising a storage vessel and a capillary tube, wherein dimensions of said storage vessel and capillary tube are selected to achieve a maximal change in hydrostatic pressure during viscosity measurement, and wherein said storage vessel exhibits changes in cross-section to permit simultaneous determination of density of a liquid at preset intervals.

15. A capillary viscometer according to claim 14, wherein said changes in cross-section are cross-section reductions produced by insertion of an element into said storage vessel, said storage vessel being of cylindrical shape.

16. A capillary viscometer for liquids comprising a storage vessel and a capillary tube, wherein dimensions of said storage vessel and capillary tube are selected to achieve a maximal change in hydrostatic pressure during viscosity measurement, and wherein the axis of said storage vessel and/or the axis of said capillary tube are arranged at an angle to the perpendicular.

17. In a process for determining the viscosity of a Newtonian liquid with a capillary viscometer, comprising a storage vessel and a capillary tube, wherein said liquid flows from said storage vessel through said capillary tube, the improvement wherein:

the flow rate of liquid through said capillary tube changes with time, the change in the rate of flow of liquid through the viscometer is measured whereby viscosity of the liquid can be determined by the Hagen-Poiseuille law, and in measuring the change in the rate of flow of liquid, the length of time required for each of a plurality of preset liquid volumes required to pass through preset measuring points is measured.

* * * * *

UNITED STATES PATENT AND TRADEMARK OFFICE
CERTIFICATE OF CORRECTION

PATENT NO. : 5,365,776
DATED : 11/22/94
INVENTOR(S) : Jochen K. LEHMANN et al.

It is certified that error appears in the above-indentified patent and that said Letters Patent is hereby corrected as shown below:

Claim 12; column 12, line 8: Delete line 8 and replace with:

$$-- k \text{ is } \frac{r^4 \cdot g \cdot \rho \cdot \pi}{8 \cdot \eta \cdot A \cdot l};$$

X is mass or volume;

r is radius of the capillary;

$\rho$ is density of the liquid;

A is cross-sectional area of the storage vessel;

UNITED STATES PATENT AND TRADEMARK OFFICE
CERTIFICATE OF CORRECTION

PATENT NO. : 5,365,776
DATED : 11/22/94
INVENTOR(S) : Jochen K. LEHMANN et al

It is certified that error appears in the above-indentified patent and that said Letters Patent is hereby corrected as shown below:

l  is length of the capillary;

η  is dynamic viscosity coefficient; and g  is acceleration due to gravity. - -

Signed and Sealed this

Eighteenth Day of April, 1995

Attest:

BRUCE LEHMAN

*Attesting Officer*

*Commissioner of Patents and Trademarks*